United States Patent [19]

Furlong et al.

[11] 4,240,419

[45] Dec. 23, 1980

[54] BREATHABLE GAS DELIVERY REGULATORS

[75] Inventors: Owen D. Furlong, West Coker; Robin H. Thring, Yeovil, both of England

[73] Assignee: Normalair-Garrett (Holdings) Limited, Yeovil, England

[21] Appl. No.: 945,477

[22] Filed: Sep. 25, 1978

[30] Foreign Application Priority Data

Sep. 26, 1977 [GB] United Kingdom ............... 40056/77

[51] Int. Cl.[3] .............................................. A61M 16/00

[52] U.S. Cl. ........................... 128/204.23; 128/204.26

[58] Field of Search ............. 128/142 R, 142.2, 142.3, 128/142.5, 203, 209, 210, 145.8, 145.5, 145.6, 204.23, 204.26

[56] References Cited

U.S. PATENT DOCUMENTS

| | | | |
|---|---|---|---|
| 3,368,555 | 2/1968 | Beasley | 128/145.8 |
| 3,875,957 | 4/1975 | Veit | 128/142.2 X |
| 4,057,059 | 11/1977 | Reid et al. | 128/145.8 |
| 4,072,148 | 2/1978 | Munson et al. | 128/142.2 |
| 4,141,356 | 2/1979 | Smargiassi | 128/145.8 |
| 4,148,311 | 4/1979 | London | 128/142.2 |

*Primary Examiner*—Harry N. Haroian
*Attorney, Agent, or Firm*—Larson, Taylor and Hinds

[57] ABSTRACT

The invention provides a breathable gas regulator of the demand type for use with a low supply pressure (10 p.s.i or less) gas source.

The regulator requires no greater demand effort on the part of a user than is required with present-day regulators of the same type which operate with much higher pressure (70 p.s.i. and above) gas sources, and it requires ducts, diaphragms and valves of no greater size than are required by present-day regulators. This is achieved by inclusion of a servo valve that is actuated by a fluidic amplifier arrangement responsive to the user's breathing pressure.

In an embodiment of the invention particularly suited for use by an aviator, the regulator includes a pneumatically operated mixing valve arrangement for automatically varying, according to altitude, the proportions of, say, oxygen and air supplied to the demand valve of the regulator, and the mixing valve arrangement includes a fluidic gas concentration sensor.

15 Claims, 3 Drawing Figures

Figure 1:
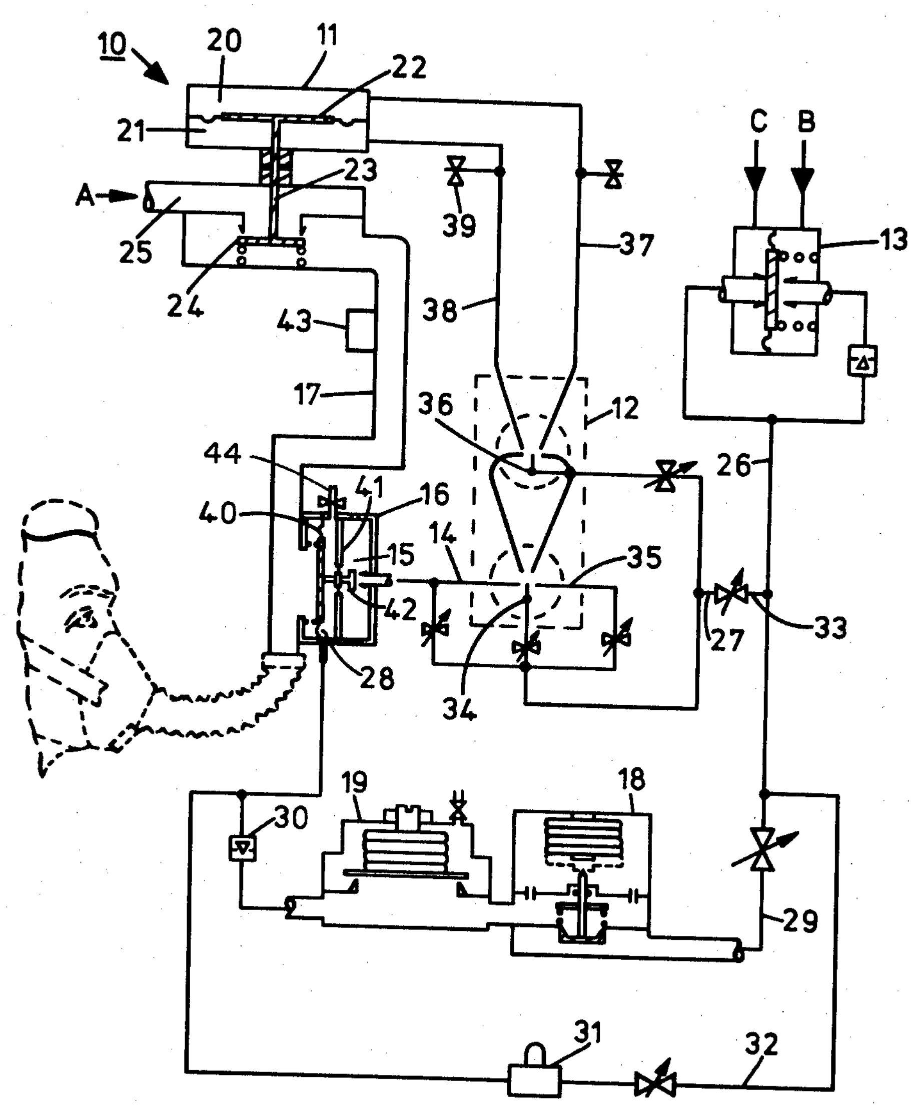

| FLIGHT CONDITION | FORCE BALANCE STATUS OF MIXING VALVE DRIVE | MIXING VALVE POSITION | |
|---|---|---|---|
| | | OXYGEN PORT | AIR PORT |
| **CONDITION 1** | | | |
| REGULATOR NOT IN USE | GM, AP ZERO; ← S | FULL OPEN | FULL SHUT |
| **CONDITION 2** | | | |
| GROUND LEVEL UP TO ALTITUDE AT WHICH OXYGEN ENRICHMENT IS ABOUT TO COMMENCE | GM ZERO; AP →; ← S | FULL SHUT | FULL OPEN |
| **CONDITION 3** | | | |
| LOW ALTITUDE WITH SMALL PERCENTAGE OF OXYGEN ENRICHMENT | GM →; AP →; ← S | JUST OPEN | NEARLY FULLY OPEN |
| HIGH ALTITUDE WITH HIGH PERCENTAGE OF OXYGEN ENRICHMENT | GM →; AP →; ← S | NEARLY FULLY OPEN | JUST OPEN |
| **CONDITION 4** | | | |
| HIGH ALTITUDE WITH MAXIMUM OXYGEN | GM NULLIFIED BY OPENING RELIEF VALVE; AP →; ← S | FULL OPEN | FULL SHUT |
| **CONDITION 5** | | | |
| MANUAL BLEED OPEN AT ANY ALTITUDE TO GIVE FULL OXYGEN | GM, AP NULLIFIED BY OPENING BLEED VALVE; ← S | FULL OPEN | FULL SHUT |

S - SPRING FORCE

AP - ABSOLUTE PRESSURE REFERENCE SENSOR FORCE

GM - GAS CONCENTRATION SENSOR FORCE

FIG. 3

BREATHABLE GAS DELIVERY REGULATORS

This invention relates to breathable gas delivery regulators of the demand type (that is, regulators that include a flow delivery valve ("demand valve") responsive to a user's breathing cycle to deliver breathable gas when required for inhalation) and while generally applicable to regulators to this type is especially applicable to those adapted to deliver a gaseous mixture.

In the demand type of breathable gas delivery regulator it is usual for the demand valve to be operated by a servo system, the inhalation and exhalation pressure of the user's breathing cycle being applied to a diaphragm adapted to actuate a pilot valve controlling a closing pressure behind the demand valve in such manner that the latter is allowed to open to deliver breathable gas during the inhalation phase of the breathing cycle.

It is the current practice to supply oxygen to an aviator's breathable gas delivery regulator at a relatively high pressure of, say, 70 p.s.i. Such a supply pressure permits the use of small ducts and demand valve components, so enabling the regulator to have reasonably small physical dimensions. However certain desirable oxygen sources, such as airborne molecular sieve oxygen generating systems, provide a low supply of, say, 10 p.s.i., or thereabouts, and if such a source were to be used with the present design of regulator, the latter would required to be unacceptably enlarged in order to accommodate ducts and components of sufficient size to pass the required oxygen flow to the user during the period of each inhalation phase.

Therefore it is an object of the invention to provide a demand type breathable gas delivery regulator that will operate satisfactorily with considerably lower gas supply pressures than has been the practice hitherto.

Accordingly, the present invention provides a breathable gas delivery regulator comprising a gas inlet for receiving a breathable gas and a gas outlet for connection to a user, a demand valve controlling communication between said gas inlet and said gas outlet, a pressure sensor for sensing the user's breathing pressure, and a servo mechanism for operating the demand valve in response to breathing pressure signals from said pressure sensor, characterized in that said servo mechanism comprises a fludic amplifier having an output to an actuator for the demand valve and a control port connected for response to breathing pressure signals from the pressure sensor.

In one form of the invention the pressure sensor comprises a vave-operating diaphragm exposed on one side to said gas outlet to sense the user's breathing pressure, and on its other side to a biassing pressure chamber, and the regulator includes bias pressure-adjusting means for adjusting the pressure in said biassing pressure chamber in response to changes in ambient pressure.

The bias pressure-adjusting means preferably comprise a safety pressure regulator responsive to ambient pressure to open a pressure line to said biassing pressure chamber when ambient pressure falls to a first preset value, thereby to apply a bias pressure to said biassing chamber, and a pressure breathing regulator responsive to ambient pressure and adapted progressively to increase the said bias pressure with decreasing ambient pressure.

The pressure breathing regulator may be adapted to commence increasing the bias pressure in response to ambient pressure falling to a second preset value lower than said first value.

Preferably the biasing pressure chamber has a restricted vent to ambient and the pressure breathing regulator controls a restricted vent to ambient from the pressure line downstream of the safety pressure regulator.

In an embodiment of the invention a breathable gas delivery regulator includes a diverter valve having inlet connections for principal and alternative pressurised gas supplies, and a gas outlet connected to deliver driving gas to the fluidic amplifier, the diverter valve being adapted normally to direct gas from the principal supply to the gas outlet but to isolate the principal supply inlet connection and to direct gas from the alternative supply to the gas outlet when the pressure of the alternative supply exceeds that of the principal supply by a predetermined amount.

A breathable gas delivery regulator in accordance with the invention may include breathable gas selection means connected to the gas inlet and adapted to receive two different breathable gases from respective sources thereof and to deliver to the gas inlet one or the other or a mixture of the breathable gases.

The breathable gas selection means may include means responsive to ambient pressure for determining the gas or gas mixture delivered to sid gas inlet, and may comprise a mixing chamber having an outlet connected to the gas inlet, and an access to each of the sources controlled by a proportioning valve resiliently biassed towards closing the access to one source and movable towards closing the access to the other source, while opening the access to said one source by a pressure-responsive movable wall arrangement exposed to a pressure difference significant of ambient pressure.

The pressure-responsive movable wall arrangement may be responsive to the difference between ambient pressure and an absolute pressure reference pressure.

According to the present invention one form of absolute pressure sensor comprises a high-recovery venturi and means for inducing a choked flow of ambient air therethrough via a passage of constant cross-section having a tapping for detecting the pressure in said passage as said absolute pressure reference pressure.

The flow-inducing means may comprise an ejector pump downstream of the venturi and operated by a jet of gas derived from a breathable gas supply.

A breathable gas delivery regulator in accordance with the present invention may include means for detecting the composition of the gas mixture delivered to the gas inlet and for generating a pressure signal significant of the content of gas from one source in the mixture and for applying this as a regulating feedback signal to ambient pressure-responsive means determining the gas mixture composition.

The gas mixture composition-detecting means preferably comprise a fluidic gas composition sensor.

The movable wall arrangement may be adapted to summate the pressure difference significant of ambient pressure with the pressure signal significant of the content of gas from said one source in the said gas mixture.

Figure 2:
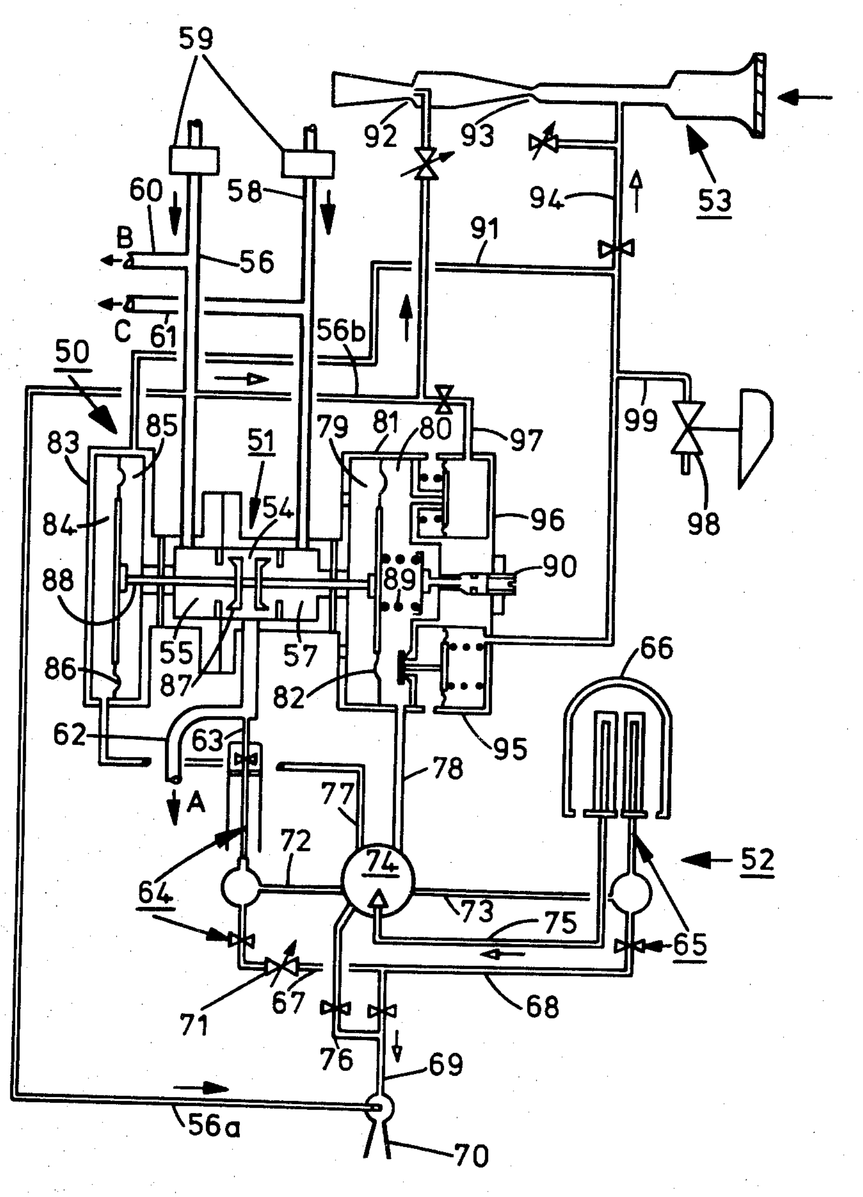

The invention will be more readily understood from the following description of an aviator'gas mixing and delivery regulator embodying the invention and illustrated in the accompaying drawings, in which:

FIG. 1 schematically illustrates a fluidic servo-operated demand valve and supplementary pressure regulating devices of the regulator;

FIG. 2 schematically illustrates gas mixing control means that conjoin with and feed the demand valve of FIG. 1; and FIG. 3 diagrammatically illustrates the status of the pressure-responsive elements and valve head of the mixing valve of the regulator, during various conditions of flight of an aircraft carrying the regulator.

The demand valve and supplementary devices shown in FIG. 1 have three gas inlet connections A, B and C that are connected to similarly designated connections of the gas mixing control means shown in FIG. 2. Connection A serves to connect the gas mixture outlet of the gas mixing means of FIG. 2 to the gas inlet to the demand valve, connection B is an inlet for pressurised air that provides principal power for servo operation of the demand valve, whereas connection C is an inlet for pressurised oxygen that provides alternative power for servo operation of the demand valve.

FIG. 1 shows schematically a servo-operated demand valve arrangement 10 including an actuator 11 that is connected to a two-stage fluidic amplifier 12 that is driven by air or oxygen received through connection B or C, respectively, by way of an automatically operable diverter valve 13 that connects the amplifer 12 to connection B whenever there is adequate air pressure at that connection. One control port, 14, of the fluidic amplifier 12 is arranged to communicate with a vent by way of a pad valve 15 that forms part of a pressure sensor unit 16 positioned on an outlet duct 17 of the demand valve arrangement 10 and that is responsive to pressure in the duct 17 as generated by the breathing of the user aviator. Safety pressure and pressure breathing regulators 18, 19 respectively are associated with the demand valve arrangement 10 to meet safety and physiological requirements of the user aviator during flight through the operational altitude range of the aircraft carryng the regulator.

The actuator 11 of the demand valve arrangement 10 comprises a chamber that is divided into two sub-chambers 20, 21 by a flexible diaphragm 22 from which extends a push rod 23 that is in contact with a demand valve 24. The valve 24 controls gas flow through the demand valve arrangement 10 from the connection A of an inlet duct 25 to the outlet duct 17.

The fluidic amplifier 12 is of known two-stage type and is connected to receive pressurised air or, in the event of failure of the air supply, pressurised oxygen, from the automatically operable diverter valve 13. This valve 13 comprises a diaphragm valve arranged to close either the oxygen flow path or the air flow path and is biassed by a spring towards closing the oxygen flow path. The air flow path includes a non-return valve. An outlet conduit 26 from the diverter valve 13 is connected to the fluidic amplifier 12 by a duct 27 and by two routes to a biassing pressure chamber 28 of the sensor unit 16. One of these two routes is by way of a duct 29 that includes the safety pressure and pressure breathing regulators 18, 19, respectively and a non-return valve 30, whereas the other route is by way of a ground test valve 31 that obturates a by-pass duct 32; the ducts, 27, 29 and 32 each include a variable flow adjuster such as shown at 33 in the duct 27. The duct 27 has branches respectively feeding a power jet 34 and control ports 14, 35 of the first stage of the fluidic amplifier 12, and a power jet 36 of the second stage thereof. Each branch of the duct 27 includes a variable flow adjuster. The amplifier 12 has two outputs 37, 38 connected respectively to the sub-chambers 20, 21 of the demand valve actuator 11 and are provided with adjustable or fixed orifice vents such as shown at 39.

The safety pressure regulator 18 and the pressure breathing regulator 19 are of known type and mode of operation. The regulator 18 is responsive to altitude, e.g. by sensing cabin pressure, and is arranged to open or close the duct 29, whereas the regulator 19 is also responsive to altitude (e.g. cabin pressure) but is arranged to control a restricted vent path from the duct 29.

The pressure sensor unit 16 comprises a housing that includes the biassing pressure chamber 28 formed between a rolling diaphragm 40, that is exposed to pressure in the outlet duct 17 of the demand valve arrangement, and a wall 41 of which part is flexible and carries the valve element 42 of th pad valve 15. The rolling diaphragm 40 is urged by a spring to bear on the end of the stem of the valve element 42, which projects through the flexible portion of the wall 41, thereby tending to close the pad valve 15. The biassing pressure chamber 28 is provided with an adjustable or fixed orifice vent 44.

An over-pressure relief valve 43 is provided to prevent over-pressure occurring in the outlet duct 17 of the demand valve arrangement 10.

The gas mixing control means schematically illustrated in FIG. 2 comprises a mixing valve arrangement 50 that includes a proportioning valve 51 operable in one sense by means that are responsive to signals respectively provided by a fluidic gas concentration sensor arrangement 52 and by an absolute pressure reference device 53, and in the opposite sense by a low rate spring 89.

The mixing valve arrangement 50 comprises a mixing chamber 54 interposed between inlet chambers 55, 57 and to which the mixing chamber is connected by respective access ports having circumscribing valve seats exposed to the interior of the mixing chamber 54. Sensing chambers 81, 83 are arranged outboard of the inlet chambers 57 and 55, respectively. The inlet chamber 55 connects with an air supply duct 56 whereas the inlet chamber 57 connects with an oxygen supply duct 58. The ducts 56, 58 each include a pressure reducing valve 59 and have branch ducts 60, 61, respectively, extending to the connections B, C, respectively, to the diverter valve 13 (FIG. 1). An outlet duct 62 connects the mixing chamber 54 with the inlet duct 25 of the demand valve arrangement 10 by way of connection A (FIG. 1) and also provides a gas mixture sampling outlet 63 that feeds a capillary/orifice sensor assemblage 64 of the gas concentration sensor arrangement 52. The capillary of the assemblage 64 is shielded over its length by a tubular cowl.

The gas concentration sensor arrangement 52 is of known type and includes a second capillary/orifice sensor assemblage 65 arranged to sample ambient (cabin) air for reference by way of filter means 66 utilising, for instance, molecular siever 4A material to remove water and carbon dioxide from the sampled air. The two sensor assemblages 64, 65 are conjoined by fluid lines 67, 68 that are connected by a tee connection to a suction line 69 of aspirator means 70. Fluid line 67 includes a variable flow restrictor 71. Sensing lines 72, 73 extend from the respective sensor assemblages 64, 65, to a laminar flow fluidic amplifier 74 which is arranged to receive ambient air by way of a duct 75 that originates in the filter means 66. A suction line 76 containing a fixed flow orifice connects the amplifier 74 with the aspirator means 70, and signal output ducts 77, 78 of the amplifier connect with sub-chambers 84, 80 of the two sensing chambers 83, 81 respectively, of the mixing valve arrangement 50. The aspirator means 70 is connected by way of a branch duct **56*a* to the air supply duct 56**.

The sub-chamber 80 is formed by division of the sensing chamber 81 with a flexible or rolling diaphragm 82, and the sub-chamber 84 is formed by division of the sensing chamber 83 with a flexible or rolling diaphragm 86. A double valve head 87 is co-operable with the two valve seats disposed within the mixing chamber 54. The valve head 87 is carried on a spindle 88 that extends through the chambers 54, 55, 57 and contacts the diaphragms 82, 86 in the sensing chambers 81, 83. The low rate spring 89, having a threaded adjuster 90, is arranged to urge the valve head 87 towards closing the air inlet access port (leftwardly in FIG. 2). The sub-chamber 79 in the sensing chamber 83 is open to ambient (cabin) pressure whereas the sub-chamber 85 is connected by way of a restricted conduit 91 to a static pressure connection of the absolute pressure reference device 53.

The absolute pressure reference device 53 is designed for operation by a low pressure jet pump 92 and to this end comprises a generally tubular body having a bell-mouth entry to a high recovery venturi 93 arranged to operate in a choked condition. Driving air is supplied to the jet pump 92, which is incorporated at the downstream end of the device 53, from the air supply duct 56 by way of a branch duct **56*b*. An absolute pressure tapping 94, that has an adjustable bleed, connects the device 53 with the conduit 91 and also with a vent valve 95 located on a wall of the sub-chamber 80. The vent valve 95** includes a diaphragm arrangement that is responsive to the difference between absolute and ambient (cabin) pressures.

Another vent valve 96 is similarly located on the wall of the sub-chamber 80 and is connected by a restricted conduit 97 to the air supply branch duct **56*b*. The vent valve 96** includes a diaphragm arrangement that is responsive to the difference between ambient (cabin) pressure and the reduced supply air pressure.

An overriding selector valve 98 is provided in a vent line 99 interconnecting with the absolute pressure tapping 94 in order to provide for 100% oxygen delivery from the regulator when desired.

In operation of the described embodiment, pressurised air and oxygen are suplied separately to the regulator from convenient sources, such as a compressor stage of an engine of an aircraft and a liquid oxygen converter system or an onboard oxygen generating system. Both the air and oxygen are reduced to a pressure of, say, 10 p.s.i. by the pressure reducing valves 59 disposed in the respective air and oxygen sypply ducts 56, 58. Airr is fed to the inlet chamber 55 and oxygen to the inlet chamber 57, from which chambers both gases can flow to the mixing chamber 54 by way of the access ports in the walls separating the chambers, under the control of the double valve head 87. Air and oxygen at the pressures in ducts 56, 58 are also separately fed via branch ducts 60, 61 respectively, to the diverter valve 13 where, owing to the biassing provided by the spring in that valve, oxygen is prevented from passing while the air is available. The air, in normal operation, passes from the diverter valve 13 by way of the non-return valve, the outlet conduit 26 and duct 27 to feed the two-stage fluidic amplifier 12 and, by way of duct 29, towards the biassing pressure chamber 28 of the pressure sensor unit 16 associated with th demand valve outlet duct 17; however the air is prevented from reaching the chamber 28 by the safety pressure regulator 18 when the valve thereof is closed, for instance when the ambient (cabin) pressure altitude is below, say, 12,000 feet, and (except for test purposes) by the ground test valve 31 in the by-pass duct 32. Air is also supplied by way of the branch air supply ducts **56*a*, 56*b* to drive the aspirator means 70 and the jet pump 92 of the absolute pressure reference device 53, respectively, and is further supplied through the restricted conduit 97 to apply a closing pressure to the vent valve 96**.

The aspirator means 70 induces a suction in lines 69 and 76, the suction in line 76 inducing a power jet to obtain in the laminar flow fluidic amplifier 74, this power jet being derived from cabin air drawn through the filter 66 and the duct 75. Suction in the line 69 draws cabin air as a reference gas through capillary/orifice sensor assemblage 65 by way of line 68, and a sample of mixed gas through the corresponding assemblage 64 by way of line 67. The tubular cowl about the mixed gas sampling capillary prevents the ingress of air thereto whilst maintaining ambient (cabin) pressure thereabout. The sensing lines 72, 73, that extend from the small chambers seen in the capillary/orifice sensor assemblages provide control of the reduced pressures induced in the signal output ducts 77, 78. The gas concentration sensor arrangement 52 is preset to give balanced output signals, when comparing identical gases, say air, by adjustment of the variable flow restrictor 71.

The absolute pressure sensor device 53, by means of its jet pump 92, induces ambient (cabin) air to flow through it in the generation of an absolute pressure reference signal. The reference is provided as a negative pressure or suction obtained by the tapping 94 sensing pressure in a parallel section of the device 53 situated between the bell-mouth entry and the high recovery venturi 93, with the venturi operating in a choked condition. The absolute pressure reference signal is sensed in the control chamber of the vent valve 95 by way of the tapping 94 and in the sub-chamber 85 by connection to tapping 94 through the conduit 91, while ambient pressure exists in sub-chamber 79. The outer sub-chambers 80, 84, sense the pressures obtaining in the signal output ducts 78, 77, respectively, of the gas concentration sensor 52. Thus, during operation, a suction pressure exists in sub-chamber 85 and a positive pressure relative thereto in sub-chamber 79, while suction pressure exists in chambers 80, 84. The pressures in the chambers 80, 84 are equal when the mixing valve arrangement 50 is passing only air but become unequal when oxygen is also passed, the chamber 80 then sensing the lower pressure.

In ground level and low altitude conditions, where oxygen enrichment is not required, the combined pressure effect of the absolute pressure reference in sub-chamber 85 overcomes the force exerted by the spring 89 so that the oxygen access port to the mixing chamber 54 is closed by the valve head 87 and only air is supplied to the demand regulator 10 from the mixing valve arrangement 50.

With increasing altitude, where oxygen enrichment becomes necessry, the absolute pressure reference signal decreases in value (i.e. becomes less negative) and consequently has a reducing effect in overcoming the force of spring 89 so that the spring commences to expand and thereby gradually moves the proportioning valve 51 so that the valve head 87 opens the oxygen access port to the mixing chamber 54. Upon delivery of oxygen-enriched air, the capillary/orifice sensor assemblage 64 produces a control signal that is unequal to that of assemblage 65, whereby a pressure difference appears in the output ducts 77, 78 of the fluidic amplifier 74 and the pressure increases (i.e. becomes less negative) in sub-chamber 84 relative to that in sub-chamber 80, thereby causing the spring 89 to be brought to a pressure balanced condition, so checking the movement of the valve head towards opening the oxygen access port and countering the excessive proportion of oxygen in the gas mixture that would otherwise result.

At ambient (cabin) altitudes where it is necessary that only oxygen is supplied to the demand regulator 10 the absolute pressure reference signal is so low in value of negative pressure that the suction pressure in the sub-chamber 85 and the control chamber of vent valve 95 can no longer restrain, respectively, the spring 89 that acts on the proportioning valve 51, nor the spring of the vent valve. Upon the vent valve 95 opening sub-chamber 80 to ambient, the pressure thereof becomes effective on the diaphragm 82 to assist the compression spring 89 to drive the proportioning valve 51 to close the valve head 87 firmly about the air access port to the mixing chamber 54.

The rolling diaphragms 82, 86 are so sized in relation to the rate of the spring 89 that for altitudes where oxygen-enriched air is required to pass to the demand valve arrangement 10, the mixing valve arrangement, in response to the altitude signal from the absolute pressure reference sensor as described, tends to deliver a slight excess to requirement of oxygen in the gas mixture. This excess is then countered by the gas concentration sensor arrangement 52, the extra oxygen in the mixture as compared with air causing unbalancing of the control signals in the sensing lines 72, 73, so that the output signals of the amplifier 74 are also unbalanced, a difference of pressure occurring in the output ducts 77, 78 and consequently in the sub-chambers 80, 84 so that the rolling diaphragms 82, 86 are subject to the effect of this difference in pressure to supplement the altitude-significant force opposing the spring 89 and thereby limit the movement of the valve head 87 to pass slightly less oxygen, that it otherwise would, to the mixing chamber 54.

During normal operation of the regulator, pressurised air is fed into and maintained in the control chamber of the vent valve 96 by way of restricted conduit 97, while suction as already mentioned is maintained in the control chamber of the vent valve 95 by way of tapping 94 which senses the absolute pressure reference, whereby the two vents of the sub-chamber 80 of the sensing chamber 81 are held closed. However, in the vent of the loss or partial loss of the absolute pressure reference signal, for instance as a result of a damage leak, not only does the suction in sub-chamber 85 of sensing chamber 83 reduce and allow the spring 89 to move the valve head 87 towards fully opening the oxygen access to the mixing chamber 54 as in response to a normal increase in altitude, but suction in the control chamber of the vent valve 95 is also reduced so that the vent valve is opened and the signal pressure in sub-chamber 80 is rapidly destroyed by the ingress of ambient (cabin) air, thereby speeding the movement of the valve head 87 and so giving a higher rate of response to the fall in absolute pressure signal value.

In the event of loss of partial loss of the pressurised air supply, although the absolute pressure reference signal would be affected with similar results to those just described, a direct and more rapid response action is obtained by the loss of pressure in the control chamber of the vent valve 96 which allows the valve to open and produce the same effect as opening of the vent valve 95.

It will be seen, also, that by operating the overriding selector valve 98 to bleed the absolute pressure sensing tapping 94, the vent valve 95 is caused to open and cause the valve head 87 to move to the position giving maximum oxygen access to the mixing chamber 54.

Referring to FIG. 1, air, or a mixture of air and oxygen, or pure oxygen as appropriate to a pertaining ambient (cabin) altitude or as chosen by the setting of valve 98 passes to the upstream side of the demand valve 24 from the mixing valve arrangement 50 by way of the outlet duct 62 and connecton A to the inlet 25 of the demand valve arrangement 10, where it is held until a demand is made by the user. The fluidic amplifier 12 is fed with pressurised air from the conduit 26 by way of the duct 27 to the power jets and control ports of the amplifier. While the pressure sensor unit 16 is at rest, the pad valve 15 therein is closed under the influence of the spring acting on the diaphragm 40 so that air fed to the control port 14 is constrained to deflect the first stage power jet 34 to the right in the drawing, thereby deflecting the power jet 36 oppositely to the left in the second stage and so applying air power to sub-chamber 21 on the underside of the flexible diaphragm 22 in actuator 11 to the demand valve 24 in the closed position.

Assuming a low ambient (cabin) altitude, say below 12,000 feet, when the two ducts 29, 32 conveying pressurised air to the biassing pressure chamber 28 in the pressure sensor unit 16 are closed by the safety pressure regulator 18 remaining inoperative, and by the ground test valve 31, then upon inhalation by the user the diaphragm 40 of the pressure sensor unit 16 responds to the reduction in pressure in the outlet duct 17, downstream of the demand valve 24, by moving to the left in the drawing. This action opens the pad valve 15 which allows the control port 14 to bleed and so allow the pressure at control port 35 to become more effective upon the first stage power jet 34 and deflect it towards the left, producing a control jet in the second stage to deflect the power jet 36 thereof to the right and so provide an operating pressure in the sub-chamber 20 that causes the demand valve 24 to open and pass the gaseous mixture to the user. When the user thereafter ceases to inhale, the diaphragm 41 of the pressure sensor 16, under the effect of its spring, closes the pad valve whereby the control jet from control port 14 is re-established and the demand valve accordingly closes again. This repeats in response to the user's breathing cycle.

When the ambient (cabin) altitude is above the,.say, 12,000 feet safety pressure level, the capsule of the safety pressure regulator 18 expands and opens the duct 29 so that pressurised air reaches the biassing pressure chamber 28. The relative flow areas of the regulator 18 and the vents of the pressure breathing regulator 19 and the biassing chamber 28 are such that a small positive pressure occurs in the chamber 28 to bias the diaphragm 40 therein towards the left against its spring. This increases the bleed from the control port 14, thereby causing slight deflection of the first stage power jet 34 to the left and so causing the demand valve 24 to open slightly and maintain a pressure of, say, 1" WG in the outlet duct 17 and the user's mask.

At ambient (cabin) altitudes where pressure breathing is required; i.e. above, say, an altitude of 40,000 feet, the capsule of the pressure breathing regulator expands and restricts the outflow from duct 29 to the vents of the pressure breathing regulator, thereby to produce a pressure in the biassing chamber 28 that increases with increasing altitude. The results are similar to those of the operation of the safety pressure regulator, but giving a pressure downstream of the demand valve 24 that increases with increasing altitude, the pressure rising to, say, 16" WG at an altitude of 50,000 feet.

The various adjustable flow restrictors, such as shown at 33, enable the circuits of the regulator to be adjusted to obtain optimum performance thereof.

FIG. 3 tabulates the relationships of the forces arising from the low rate spring 89 and from the pressures acting upon the rolling diaphragms 82, 86 (mixing valve drive), and the position of the double valve head 87 in the mixing chamber 54, during various operating conditions.

1. When the regulator is not in use the only force being exerted is that of the spring 89 which holds the valve head 87 in a position closing the air access to the mixing chamber 54.

2. When the regulator is in use at ground level and at flight levels up to an ambient (cabin) altitude at which oxygen enrichment is to commence, the altitude signal, i.e. suction, generated by the absolute pressure device 53 acts in the sub-chamber 85 upon the rolling diaphragm 86 to produce a force that exceeds or equals that of the spring 89, so that the valve head 87 is held in a position closing the oxygen access to the mixing chamber 54 and allows unenriched air to reach the demand valve 24.

In this operating condition, the capillary/orifice sensor assemblages 64, 65 both sensing air, i.e. the pressurised air as supplied to the regulator and the air delivered thereby, so that that two signal outputs 77, 78 from the laminar flow amplifier 74 are, substatially, the same and so have no net effect on the rolling diaphragms 82 and 86.

3. When the regulator is in use at slightly higher ambient (cabin) altitudes, a small proportion of oxygen is required to enrich the air delivered by the regulator. However, at such altitudes the signal, i.e. suction, generated by the absolute pressure reference device 53 is less than that obtaining at lower altitudes and consequently the effect of this signal on rolling diaphragm 86 is reduced, permitting the spring 89 to move the valve head 87 slightly to open the oxygen access to the chamber 54 and to reduce the access for air. The gas concentration sensor arrangement 52 senses the oxygen excess in the mixture and a difference in pressure signal output from the amplifier 74 occurs and provides a net force on the rolling diaphragms 82, 86 that partly counters the movement of the valve head 87 in response to the falling altitude signal. As the ambient altitude increases, the progressive reduction in the absolute pressure reference signal leads to a progressive movement of the valve head 87 towards giving greater oxygen access and less air access to the mixing chamber 54.

4. At high ambient altitudes where maximum oxygen is required to be delivered by the regulator, the absolute pressure reference altitude signal becomes so low that insufficient suction is created to enable the rolling diaphragm 86 to restrain the spring 89, which moves the valve head 87 into the position that closes the air access. At the highest altitudes, the altitude signal is insufficient to hold the vent valve 95 closed so that this opens to permit the entry of ambient pressure to the sub-chamber 20, which pressure thereby becomes effective in both of sub-chambers 79 and 80, removing the influence of the signal in line 78 from the diaphragm 82 and so assisting the spring 89 to move the valve head 87 to close the air access to the mixing chamber.

5. Manual selection of a maximum oxygen delivery is obtained by operating the overriding selector valve 98 so that the absolute pressure reference signal is destroyed by connecting the spring 94 to ambient, whereupon the vent valve 95 opens and the ambient pressure becomes effective on both sides of the rolling diaphragm 82, to cause the valve head 87 firmly to close the air access and open fully the oxygen access to the mixing chamber 54, as at the highest altitudes.

It will be appreciated that various modifications and alternatives may be introduced in the described embodiment without departing from the scope of the invention: for example the vent valves 95 and 96 may be omitted, whilst a known follower diaphragm arrangement may be incorporated in the pressure sensor unit 16. Further, by appropriately orientating the regulator in an aircraft and by suitable modification of the rolling diaphragm 86 it could be arranged to provide an increased proportion of oxygen in the delivered mixture during manoeuvres of flight that create high 'g' loadings. The safety pressure regulator 18 could be modified to obviate use of a capsule, by utilising a diaphragm arrangement that is responsive to the difference between ambient (cabin) pressure and the absolute pressure reference signal. The various pressure connections to the sub-chambers may be differently arranged: for example, the pressure signals from the gas concentration sensor (amplifier 74) may be fed one to each side of one diaphragm, the absolute pressure reference signal and the ambient pressure being applied to opposite sides of another diaphragm.

What we claim is:

1. A breathable gas delivery regulator comprising a gas inlet for receiving a breathable gas and a gas outlet for connection to a user, a demand valve controlling communication between said gas inlet and said gas outlet, a pressure sensor for sensing the user's breathing pressure, and a servo mechanism for operating the demand valve in response to breathing pressure signals from said pressure sensor, characterised in that said servo mechanism comprises a fluidic amplifier having an output to an actuator for the demand valve and a control port connected for response to breathing pressure signals from the pressure sensor.

2. A breathable gas delivery regulator according to claim 1, wherein said pressure sensor comprises a valve-operating diaphragm exposed on one side to said gas outlet to sense the user's breathing pressure, and on its other side to a biassing pressure chamber, and bias pressure-adjusting means for adjusting the pressure in said biassing pressure chamber in response to changes in ambient pressure.

3. A breathable gas delivery regulator according to claim 2, wherein said bias pressure-adjusting means comprise a safety pressure regulator responsive to ambient pressure to open a pressure line to said biassing pressure chamber when ambient pressure falls to a first preset value, thereby to apply a bias pressure to said biassing pressure chamber, and a pressure breathing regulator responsive to ambient pressure and adapted progressively to increase the said bias pressure with decreasing ambient pressure.

4. A breathable gas delivery regulator according to claim 3, wherein said pressure breathing regulator is adapted to commence increasing the bias pressure in response to ambient pressure falling to a second preset value lower than said first value.

5. A breathable gas delivery regulator according to claim 3, wherein said biassing pressure chamber has a restricted vent to ambient and said pressure breathing regulator controls a restricted vent to ambient from said pressure line downstream of said safety pressure regulator.

6. A breathable gas delivery regulator according to claim 1, including a diverter valve having inlet connections for principal and alternative pressurised gas supplies, and a gas outlet connected to deliver driving gas to said fluidic amplifier, said diverter valve being adapted normally to direct gas from said principal supply to said gas outlet but to isolate said principal supply inlet connection and to direct gas from said alternative supply to said gas outlet when the pressure of the alternative supply exceeds that of the principal supply by a predetermined amount.

7. A breathable gas delivery regulator according to claim 1, including breathable gas selection means connected to said gas inlet and adapted to receive two different breathable gases from respective sources thereof and to deliver to said gas inlet one or the other or a mixture of said breathable gases.

8. A breathable gas delivery regulator according to claim 7, wherein said selection means include means responsive to ambient pressure for determining the gas or gas mixture delivered to said gas inlet.

9. A breathable gas delivery regulator according to claim 8, wherein said selection means comprise a mixing chamber having an outlet connected to said gas inlet, and an access to each of said sources controlled by a proportioning valve resiliently biassed towards closing the access to one source and movable towards closing the access to the other sourse, while opening the access to said one source by a pressure-responsive movable wall arrangement exposed to a pressure difference significant of ambient pressure.

10. A breathable gas delivery regulator according to claim 9, wherein said pressure-responsive movable wall arrangement is responsive to the difference between ambient pressure and an absolute pressure reference pressure.

11. A breathable gas delivery regulator according to claim 10, including an absolute pressure sensor comprising a high-recovery venturi and means for inducing a choked flow of ambient air therethrough via a passage of constant cross-section having a tapping for detecting the pressure in said pasage as said absolute pressure reference pressure.

12. A breathable gas delivery regulator according to claim 11, wherein said flow-inducing means comprise an ejector pump downstream of the venturi and operated by a jet of gas derived from a breathable gas supply.

13. A breathable gas delivery regulator according to claim 8, including means for detecting the composition of the gas mixture delivered to said gas inlet and for generating a pressure signal significant of the content of gas from said one source in said mixture and for applying this as a regulating feedback signal to the said ambient pressure-responsive means determining the gas mixture composition.

14. A breathable gas delivery regulator according to claim 13, wherein said gas mixture composition-detecting means comprise a fluidic gas composition sensor.

15. A breathable gas delivery regulator according to claim 9, wherein said movable wall arrangement is adapted to summate the pressure difference significant of ambient pressure with the pressure signal significant of the content of gas from said one source in the said gas mixture.

* * * * *